US011105522B2

(12) United States Patent
Kleinberger et al.

(10) Patent No.: US 11,105,522 B2
(45) Date of Patent: Aug. 31, 2021

(54) AIR TREATMENT SYSTEMS

(71) Applicant: PRODEW, INC., Marietta, GA (US)

(72) Inventors: Itamar Kleinberger, Marietta, GA (US); Shakeel Merchant, Atlanta, GA (US); Faizan Aly, Smyrna, GA (US); Paul Wilhelm, Roswell, GA (US); Kendall Palmer, Hiram, GA (US)

(73) Assignee: PRODEW, INC., Marietta, GA (US)

( * ) Notice: Subject to any disclaimer, the term of this patent is extended or adjusted under 35 U.S.C. 154(b) by 227 days.

(21) Appl. No.: 16/118,249

(22) Filed: Aug. 30, 2018

(65) Prior Publication Data

US 2019/0063763 A1    Feb. 28, 2019

Related U.S. Application Data

(60) Provisional application No. 62/552,916, filed on Aug. 31, 2017.

(51) Int. Cl.
*F24F 3/167* (2021.01)
*B01D 46/52* (2006.01)
(Continued)

(52) U.S. Cl.
CPC .............. *F24F 3/167* (2021.01); *A61L 2/022* (2013.01); *A61L 9/205* (2013.01); *B01D 46/521* (2013.01);
(Continued)

(58) Field of Classification Search
CPC ............... F24F 3/161; F24F 2003/1667; F24F 2003/1628; F24F 3/167; F24F 8/192;
(Continued)

(56) References Cited

U.S. PATENT DOCUMENTS 3,094,400 A * 6/1963 Blanton ..................... A61L 9/20
96/16
4,210,429 A * 7/1980 Golstein ..................... A61L 9/20
422/121
(Continued)

FOREIGN PATENT DOCUMENTS

WO    WO-2015072595 A1 *  5/2015  ......... B01D 53/8687

OTHER PUBLICATIONS

Moreno-Castilla et al. "Carbon-Based Honeycomb Monoliths for Environmental Gas-Phase Applications". Materials 2010, 3, 1203-1227. www.mdpi.com/journal/materials.*
(Continued)

*Primary Examiner* — Edelmira Bosques
*Assistant Examiner* — Christopher Matthew Odell
(74) *Attorney, Agent, or Firm* — Gardner Groff & Greenwald, PC (57) ABSTRACT

An air mover for forcing air through the system, a pre-treating stage with a particulate filter for removing larger contaminants from the air and an antimicrobial (e.g., copper and silver) filter for killing or damaging microorganisms, a UV chamber including an ultraviolet lamp that emits radiation and a catalytic (e.g., $TiO_2$-coated) device and a reflective (e.g., mirror-finish anodized aluminum) lining for amplifying the UV radiation for killing microorganisms, a post-UV stage including a VOC-reducing (e.g., activated-charcoal) filter for removing odors and VOCs from the air, and optionally a supply of a surface disinfectant (e.g., $ClO_2$). In example embodiments, the UV lamps and VOC filters are selected and configured for controlling microbial pathogens, and in other example embodiments they are selected and configured for removing ethylene from the air.

7 Claims, 10 Drawing Sheets

(51) Int. Cl.
*A61L 9/20* (2006.01)
*A61L 2/02* (2006.01)
*F24F 8/192* (2021.01)
*F24F 8/22* (2021.01)
*F24F 8/30* (2021.01)
*F24F 8/167* (2021.01)
*F24F 3/16* (2021.01)

(52) U.S. Cl.
CPC ............ *F24F 8/192* (2021.01); *A61L 2209/14* (2013.01); *B01D 2221/06* (2013.01); *B01D 2257/7022* (2013.01); *B01D 2257/91* (2013.01); *B01D 2259/4591* (2013.01); *B01D 2259/804* (2013.01); *B01D 2279/51* (2013.01); *F24F 8/167* (2021.01); *F24F 8/22* (2021.01); *F24F 8/30* (2021.01)

(58) Field of Classification Search
CPC ..... F24F 8/30; F24F 8/167; F24F 8/22; B01D 2221/06; B01D 2259/4591; B01D 2259/804; B01D 2279/51
USPC .......................................................... 454/187
See application file for complete search history.

(56) References Cited

U.S. PATENT DOCUMENTS

| | | | | |
|---|---|---|---|---|
| 5,225,167 A * | 7/1993 | Wetzel | ...................... | F24F 3/16 96/224 |
| 5,330,722 A | 7/1994 | Pick et al. | | |
| 5,505,904 A * | 4/1996 | Haidinger | .................. | A61L 9/20 250/435 |
| 5,811,022 A | 9/1998 | Savas et al. | | |
| 5,891,399 A * | 4/1999 | Owesen | .................... | A61L 9/20 422/121 |
| 5,997,619 A * | 12/1999 | Knuth | ....................... | F24F 8/10 96/224 |
| 6,149,717 A * | 11/2000 | Satyapal | .................. | F24F 3/166 96/16 |
| 6,322,614 B1 * | 11/2001 | Tillmans | ................... | A61L 9/20 96/16 |
| 6,503,458 B1 * | 1/2003 | Ogle | ......................... | A61L 9/12 422/120 |
| 8,293,171 B2 | 10/2012 | Haven | | |
| 9,308,492 B2 | 4/2016 | Obee | | |
| 9,782,510 B1 * | 10/2017 | Burnett | ..................... | A61L 9/205 |
| 2002/0020297 A1 * | 2/2002 | Harris | ...................... | B01D 49/00 95/273 |
| 2002/0150805 A1 * | 10/2002 | Stenersen | ............. | B01D 46/527 429/410 |
| 2005/0072308 A1 | 4/2005 | Aoyagi | | |
| 2005/0150386 A1 * | 7/2005 | Cheng | ..................... | B01D 46/10 96/223 |
| 2005/0160528 A1 * | 7/2005 | Clark | ......................... | F24F 3/16 5/506.1 |
| 2005/0271414 A1 | 12/2005 | Katayama et al. | | |
| 2006/0021302 A1 * | 2/2006 | Bernard | ................. | B01D 46/10 55/282 |
| 2006/0233683 A1 | 10/2006 | MacDonald | | |
| 2008/0092745 A1 * | 4/2008 | Tsao | .................... | B01D 46/0038 96/224 |
| 2008/0113040 A1 | 5/2008 | Doona et al. | | |
| 2008/0134538 A1 | 6/2008 | McFarland | | |
| 2009/0004046 A1 | 1/2009 | McEllen | | |
| 2009/0078911 A1 * | 3/2009 | Shibata | ...................... | A61L 9/01 252/187.21 |
| 2011/0033346 A1 | 2/2011 | Bohlen et al. | | |
| 2011/0171094 A1 | 7/2011 | Zahedi | | |
| 2012/0152632 A1 | 6/2012 | Azuma | | |
| 2013/0239803 A1 * | 9/2013 | Palmer | .................... | F24F 3/166 95/22 |
| 2014/0067130 A1 * | 3/2014 | Pillai | ..................... | H05B 47/105 700/275 |
| 2014/0157990 A1 * | 6/2014 | Piry | .......................... | A61L 9/16 96/226 |
| 2015/0202341 A1 * | 7/2015 | Ediger | ................... | B01D 53/88 422/121 |
| 2017/0246333 A1 * | 8/2017 | Carbone | .................... | A61L 9/12 |

OTHER PUBLICATIONS

"Machine Translation for WO2015072595A1". 2021.*
International Search Report and the Written Opinion of the International Searching Authority from counterpart PCT Application, PCT/US2018/48959, dated Jan. 7, 2019.
Phototronic Comprehensive Multistage Air Purification brochure from Ultravation, Inc., Poultney, Vermont, 2013.

* cited by examiner

AIR TREATMENT SYSTEMS

CROSS-REFERENCE TO RELATED APPLICATION

This application claims the priority benefit of U.S. Provisional Patent Application Ser. No. 62/552,916 filed Aug. 31, 2017, the entirety of which is hereby incorporated herein by reference for all purposes.

TECHNICAL FIELD

The present invention relates generally to the field of air treatment and purification, and more particularly to systems and methods for removal of microbial pathogens and/or contaminants for preservation of perishables.

BACKGROUND

Air purification and treatment to remove pathogens and/or contaminants from contained spaces is utilized in various applications. Such pathogens and/or contaminants commonly include microorganisms, volatile organic compounds (VOCs), ethylene, molds, odors, and other pathogens. And such contained spaces commonly include applications such as small storage rooms, large industrial warehouses, cold storage rooms, healthcare facilities, laboratories, manufacturing facilities, transport containers, agricultural facilities, food storage and processing facilities, livestock and poultry farming and processing facilities, cruise ships, child and elder care facilities, clean rooms, isolation rooms, negative pressure rooms, schools, universities, medical offices, surgical rooms, emergency rooms, waiting rooms, human transportation conveyances, ambulances and other healthcare vehicles, military and law enforcement facilities and vehicles, indoor public/private gathering places, and in other industrial, commercial and/or residential areas.

These pathogens and/or contaminants can be invisible to the naked eye, and they jump from host to host through the surrounding air. For example, they can attach themselves to airborne pollutants such as dust, pollen, and smoke, causing them to settle on surfaces and on top of other organisms. Over time these pathogens can destroy or weaken the host.

Half or more of all food produced globally may go to waste at some stage between agricultural production and consumption by individuals. A large portion of this food is lost during processing, storage and/or transportation prior to sale to the consumer. Food loss prior to sale results in wasted agricultural capabilities, labor, land, water, and energy, in addition to contributing to emissions of methane and other greenhouse gases from landfills. Without proper controls, many traditional food processing, transport and storage processes may promote the growth of pathogenic microorganisms (e.g., fungi, mold, mildew, bacteria, yeast, etc.) that may naturally or otherwise be present in, on, or around the products to be preserved. Excess growth of microorganisms can have detrimental effects on the food products or their marketability.

Furthermore, ethylene gas and other gases (carbon dioxide, etc.) are released during the harvesting, storage, and transport of fruits and vegetables, causing ripening and other changes in the texture, fragrance, and taste of produce; some produce items produce ethylene gas as part of the maturation process. If these food items must be stored, ethylene and other gases can accumulate in the storage area, causing the fruit or vegetables to ripen prematurely, over-ripen, or even rot, altering the flavor of food items, shortening product life, causing fresh flowers and buds to bloom prematurely, wilt or decay, and/or increasing the risk of explosion, which can occur at high ethylene concentrations.

Known methods of controlling pathogens include the delivery of heat for sterilization, the use of high energy/high temperature catalytic conversion systems, the use of steam or microwaves, the use of sprayed, fogged, or bubbling systems employing chemicals such as hypochlorite or peracetic acid, the injection of ozone into the air, or the use of medical grade HEPA filters. Many known methods of controlling pathogens can be harmful to people or cause corrosion of equipment. Additional methods such as photocatalytic oxidation systems using titanium dioxide and other photocatalytic substances have shown promise, but they typically require a very slow flow rate to effectively process the air and typically require much maintenance. HEPA filters trap pathogens, which may then become a source of harmful exposure at the time of unit maintenance and/or filter replacement.

Meanwhile, known methods of controlling ethylene concentrations include introduction of nitrogen and sulfur gases to induce fruits and vegetables to stop producing ethylene; however, traces of these gases may be left behind, creating potential health concerns. Other methods include using materials such as activated charcoal, silica gel, or molecular sieves and granular potassium permanganate to adsorb ethylene and other hydrocarbons; these materials can be inefficient, expensive, difficult to dispose of, and may lose effectiveness over time.

Accordingly, it can be seen that needs exist for improved systems and methods for treating and purifying air, disinfecting and controlling pathogens, and/or removing ethylene gas from produce storage areas. It is to the provision of solutions meeting some or all of these and/or other needs that the present invention is primarily directed.

SUMMARY

The present invention provides systems and methods for treating and purifying air, for disinfecting and controlling pathogens by use of a series of filters and exposure to ultraviolet radiation, and/or for preserving foods and other perishable items from decay, rot, spoilage, or disease promotion through eliminating pathogens and/or ethylene from the air surrounding the perishable items during storage and transportation. In example applications, the systems and methods of the present invention may be utilized in contained spaces ranging from small storage rooms to large industrial warehouses, cold storage rooms, healthcare facilities, laboratories, manufacturing facilities, transport containers, agricultural facilities, food storage and processing facilities, livestock farming and processing facilities, and in other industrial, commercial and/or residential areas, along with retail sales facilities, recreational and exercise centers, penal institutions, and all modes of transportation of humans and goods.

In one aspect, the present invention relates to an air-treatment system or device for controlling pathogens, the system comprising an air-moving device for delivering air from an environment and through a reaction chamber with at least one ultraviolet lamp.

In another aspect, the present invention relates to an air-purification system including an air intake end, an air-movement device forcing air through the system, a reflective chamber housing one or more ultraviolet lamps, and an air-discharge end. The ultraviolet lamps and/or other system components are selected and configured for removing pathogens from the air, thereby preventing them from settling on surfaces and establishing colonies, preventing decay, and preventing infection.

In another aspect, the present invention relates to an air-purification system including an air-intake end, a blower for moving air through the system, a reflective chamber housing one or more ultraviolet lamps, and an air-discharge end. The UVC ultraviolet lamps and/or other system components are selected and configured for removing ethylene from the air, thereby preventing stored or transported fruits, vegetables, and flowers from premature ripening.

In another aspect, the invention relates to an air-purification system or device having a series of filters that can assist in removing pathogens and particulate matter and in promoting airflow by preventing the blockage of filters or air outlets anywhere in the system. The system preferably includes a particulate filter at the air intake end that removes larger contaminants and prevents blockage of a second antimicrobial filter. The system further preferably includes one or more VOC reducing (e.g., activated-carbon) filters at the discharge end, wherein the VOC-reducing filters remove ozone, odors, or a combination thereof from the air before returning it back into a room or produce storage area.

In still another aspect, the invention relates to an air-purification system or device having a control box that houses both the particulate filter and the antimicrobial filter as well as a centrifugal blower, wherein the blower assists in moving air through the device in a direction going from the air intake end, through the control box, into the UV-lamp reflective chamber, and out through the discharge end. Further in this aspect, the outside wall of the device can include a control panel having a power switch, one or more indicator lights, and one or more meters indicating system run time, total filter usage, or more. These elements can be connected to a circuit inside the control box. In yet another aspect, the invention includes safety features such as limit switches that prevent operation of the system when one or more filters and/or the lid are not in place. This can prevent user exposure to moving parts, electrical currents, and/or ultraviolet irradiation.

In yet another aspect, the present invention relates to a system for preserving perishables. The system includes one or more ultraviolet lamps for irradiating air flowing through the system, wherein the effects of the ultraviolet lamps can be amplified via their placement into a reflective chamber or by the further inclusion of a catalytic (e.g., $TiO_2$) coated stainless steel rod that interacts with one or more ultraviolet light lamps to produce hydroxyl radicals or another form of catalyst to produce oxidizing and reactive agents. In some aspects, the UV lamps emit radiation in the UVC range; and in other aspects, the lamps emit radiation at a lower or higher UV level (e.g., shorter or longer wavelength) and may also produce ozone. In other aspects, one or more lamps of other wavelengths may be utilized, or the lamps can optionally be omitted in filter-only applications. In example applications, the system removes bacteria, microbial spores, fungi, viruses, and the like from air, thereby extending the shelf life of perishable items. In further applications, the system further removes ethylene from the air, thereby preventing premature ripening of fruits and vegetables and premature wilting of flowers and buds, among other effects. The air may also be treated to contain chemicals such as ClO2 (chlorine dioxide) to aid in cleaning of air and surfaces. In example forms, the treated air is discharged into the environment surrounding the perishables to be preserved. The perishables can be any perishable items such as flowers, produce, cannabis, seafood, meat, or other plant or animal matter.

In another aspect, the present invention relates to a method for controlling pathogens, for example in medical or healthcare facilities or mobile applications. The method preferably includes the dispensing of air that has been cleansed of pathogens through filtration, ultraviolet irradiation, and/or other methods, into a storage or transportation area or compartment containing articles (e.g., perishable food or floral items) with surfaces from which pathogens should be removed or prevented from settling, with the dispersed air optionally containing chemicals such as ClO2 (chlorine dioxide) to aid in cleaning of the air and surfaces.

In another aspect, the present invention relates to a system and/or method for treating air in conjunction with other devices such as humidification devices so that air, products and surfaces are disinfected through spraying of disinfectants by the other devices and then the present system and method keeps the air clean and void of pathogens, ethylene, VOCs, etc.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

DETAILED DESCRIPTION OF EXAMPLE EMBODIMENTS

The present invention may be understood more readily by reference to the following detailed description of example embodiments taken in connection with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-7 show an air-treatment system or device 100 according to a first example embodiment of the present invention. The air-treatment device 100 of this embodiment is specifically designed and optimized to remove microbial pathogens from the air, but it can be modified and adapted for targeting other airborne contaminants form the air, as will be understood by persons of ordinary skill in the art. As such, it will be understood that not all of the components of the example embodiments shown and described herein are required in every embodiment and application of the invention, and that one or more alternate components may be used in place of one or more of the particular example components described and shown.

Figure 1:
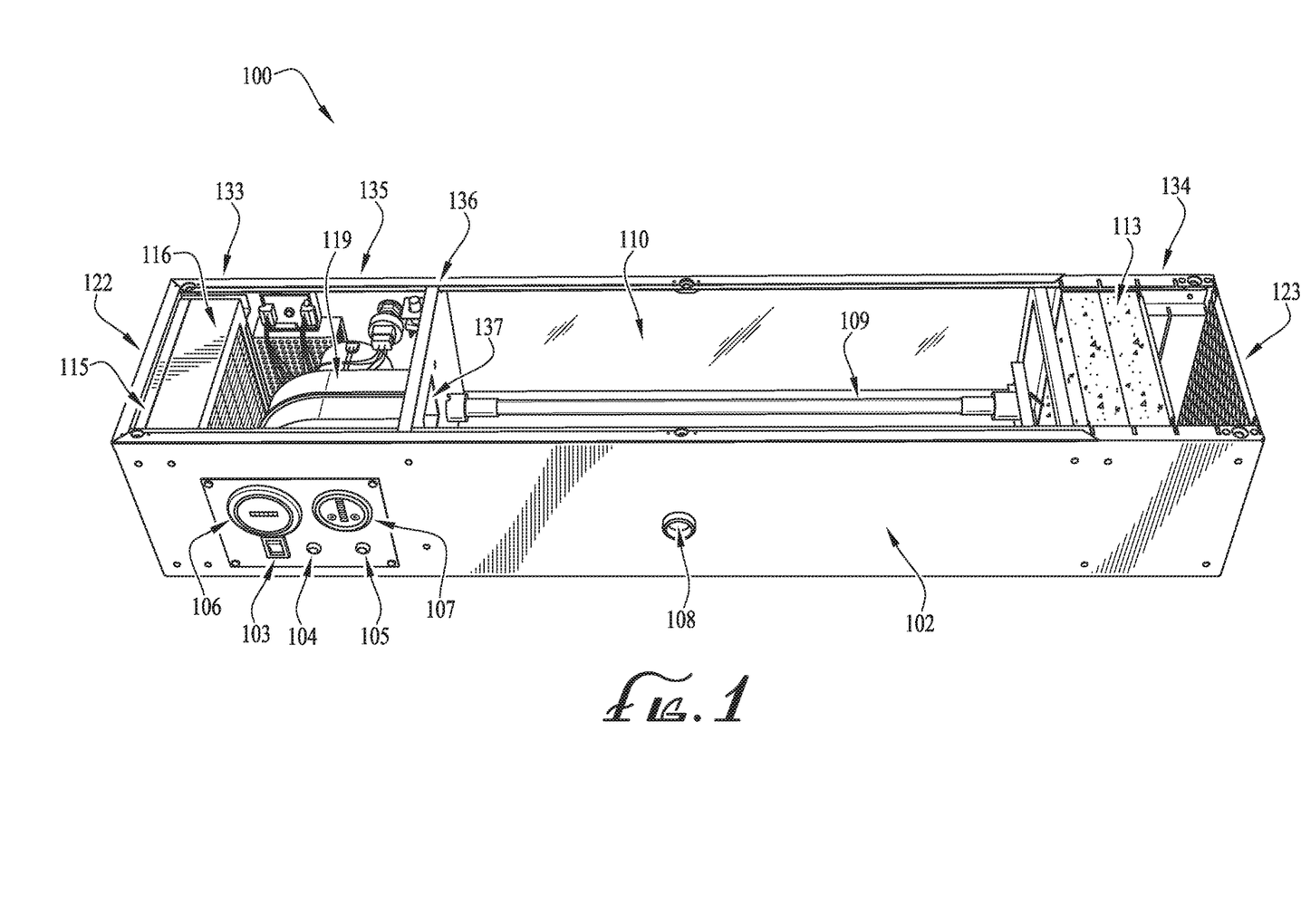
FIG. 1 is a perspective view of an air treatment device according to a first example embodiment of the present invention, with a cover panel of the housing removed to show the internal components, including an entrance treatment chamber, an intermediate UV treatment chamber, and an exit treatment chamber, configured for removing microbial pathogens from the air.

The air-treatment device 100 includes a housing 102 with an intake end 122 and a discharge end 123, an air mover 119 for forcing air through the housing from the intake to the discharge, a pre-treating chamber 133 with a particulate filter 115 for removing larger airborne contaminants and an antimicrobial filter 116 for killing or damaging microorganisms, a UV chamber 110 including an ultraviolet lamp 109 that emits radiation for killing microorganisms, a post-UV chamber 134 including a VOC-reducing filter 113 for removing VOCs and odors from the air. In some embodiments such as that depicted, the UV chamber 110 further includes a catalytic device and/or a reflective lining for amplifying the UV radiation, and/or a supply of a surface disinfectant.

Figure 2:
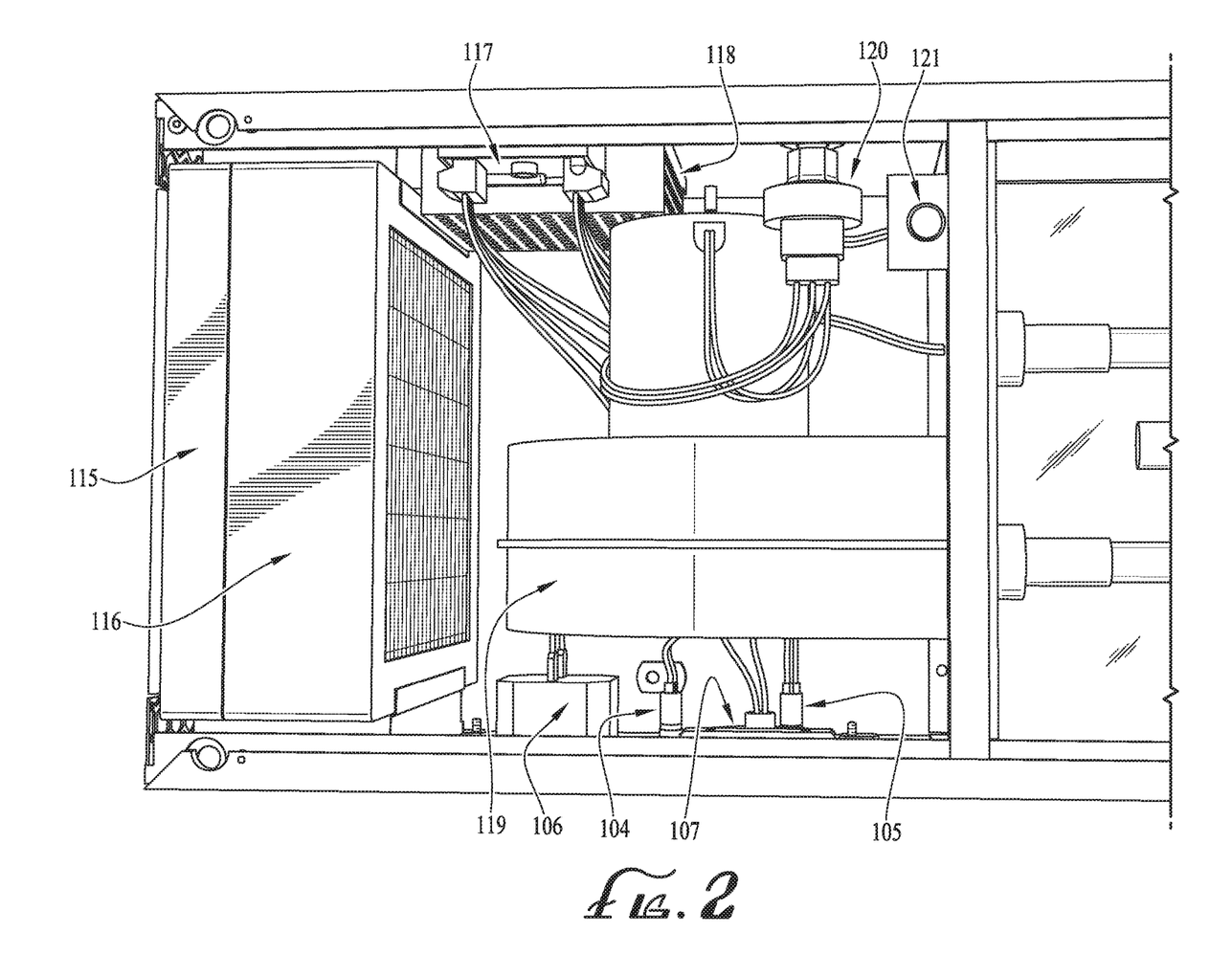
FIG. 2 is a plan view of the entrance chamber of the air treatment device of FIG. 1.
Figure 3:
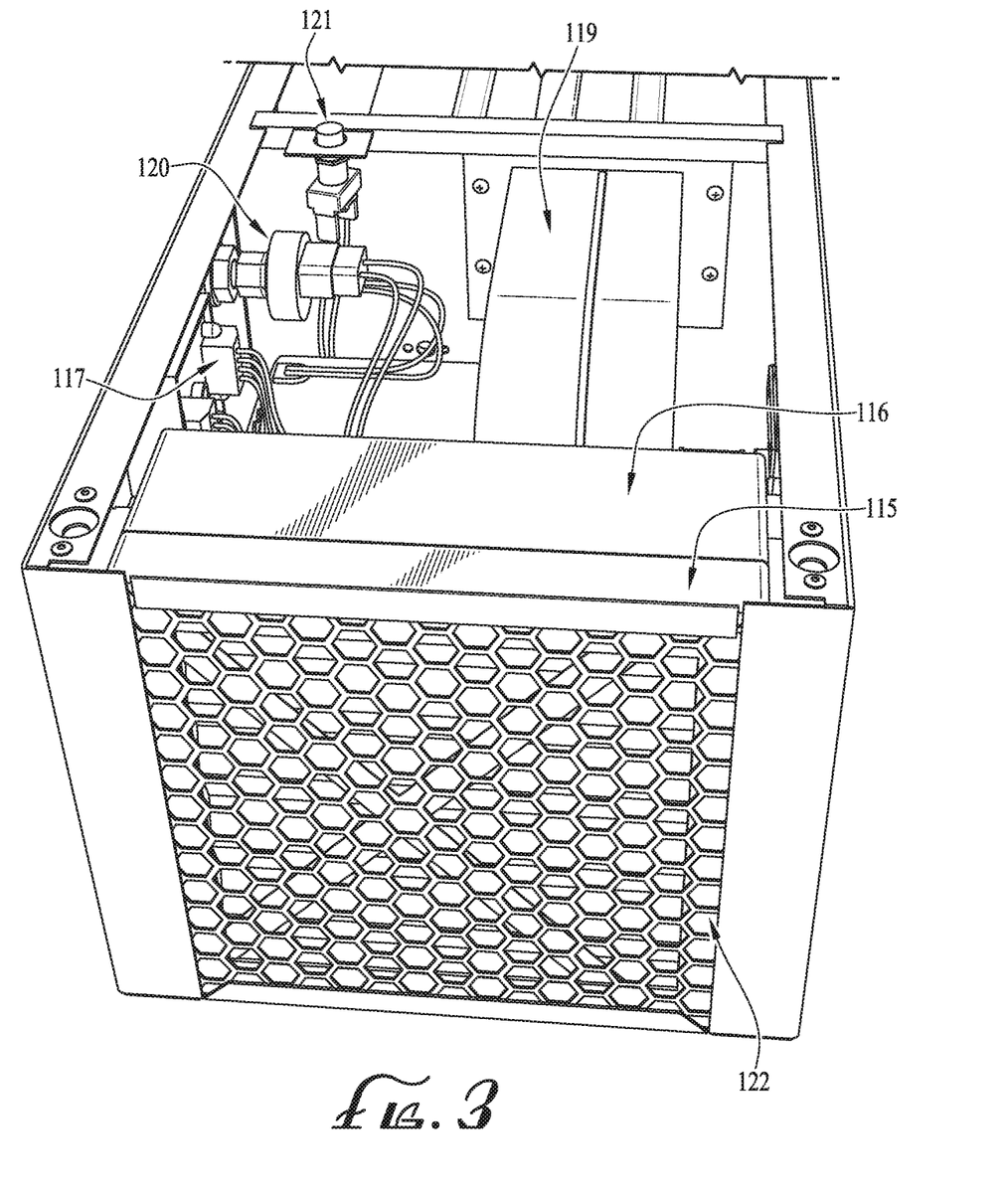
FIG. 3 is a perspective view of an intake end of the air treatment device of FIG. 1.
Figure 4:
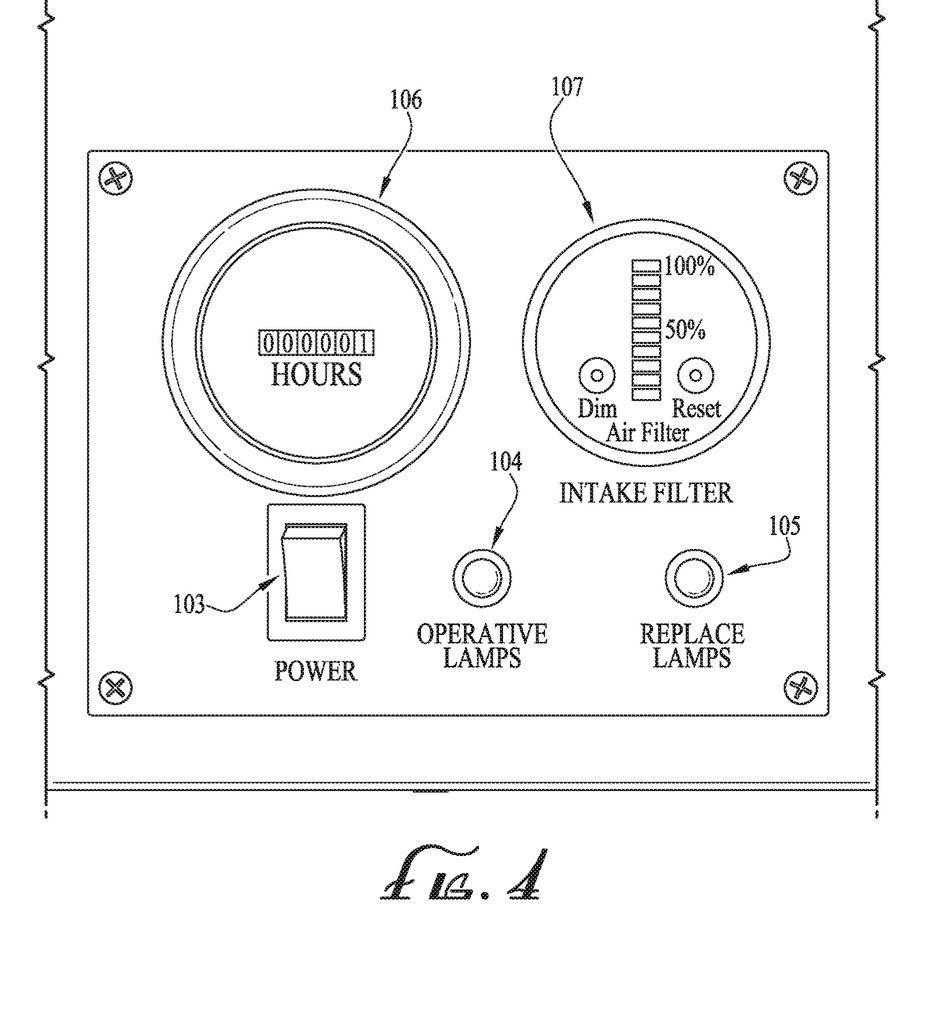
FIG. 4 is a detail view of a control panel of the air treatment device of FIG. 1.

Referring particularly to FIGS. 2-4, the air mover 119 can be of a conventional type such as a blower or fan, and is typically mounted in an air-handling chamber 135 positioned after the entrance/pre-treating chamber with the particulate filter 115 and the antimicrobial filter 116. In typical commercial embodiments, the air mover 119 is a centrifugal fan, for example a 120 V, 60 cycle fan that is capable of producing an airflow rate of approximately 140 to 150 cubic feet per minute through the pre-treating stage, the UV stage, and the post-UV stage, with airspeeds of about 437 feet per minute to about 468 feet per minute. This relatively high airflow rate and airspeed is achieved because a relatively long dwell time of the air in the device 100 is not required because of the effectiveness of the multiple air-treatment stages of achieving quick and efficient contaminant removal and microbial cell death. In other embodiments, other type of air movers with other ratings can be used depending on the intended application and desired operating parameters. In addition, the air intake end 122 and the air discharge end 123 are sized to provide a free flow of the air through them with negligible airflow resistance.

Control components are provided for operating the air mover 119 and other operational components of the air-treatment device 100. For example, additional components can include a main power supply (e.g., a power cord for connecting to a 120 V power source) and a power control 103 for example an on-off switch with overcurrent protection (e.g., an integral circuit breaker). Additional operational/control components of the device 100 can include a lamp timer 117 that counts down time to replacement of the UV lamps 109, a pressure differential sensor 120 that monitors the efficiency of the particulate filter 115, a safety switch 121 that cuts the power to the air mover 119 if the housing cover lid is not in place, and safety switches (not shown) that cut the power to the air mover 119 if one of the filters 115, 116, or 113 are not in place. A control panel can be provided with the power control 103 as well as user interface components for example an operative UV lamp indicator 104 (for indicating the UV lamp(s) is turned on), a UV lamp replacement indicator 105 (operably connected to the lamp timer 117, for indicating UV lamp 109 replacement is needed soon), a run-time meter 106 (for total elapsed running time of the air mover 119), and a filter status indicator (operably connected to the pressure differential sensor 120, for indicating particulate filter 115 replacement is needed soon) 107. A control power supply (e.g., stepped down to 24VAC) 118 is provided for operation of these additional operational and control components, which are typically all located in the air-handling chamber 135 (upstream from the UV chamber 110) with the air mover 119 (with the particulate filter 115 located upstream from the air mover 119). Also, a sight glass 108 can be provided that extends through the housing 102 and is located at the UV chamber 110 to enable a user to view operation of the UV lamp 109 from the exterior of the housing 102 to confirm proper operation.

The particulate filter 115 is selected for removing relatively large airborne particles such as dust, pollen, and other particulate and biological contaminants (e.g., 0.3 microns), in order to help clean the air and also to prevent these relatively large particles (e.g., 0.3 microns and larger) from clogging the downstream (and finer pore sized) antimicrobial filter 116 and damaging the downstream air mover 119 and other operational/control equipment. Also, the particulate filter 115 is selected for low airflow resistance, preferably to allow for a high airflow rate of about 140 to 150 cubic feet per minute, with airspeeds of about 437 feet per minute to about 468 feet per minute, through the filter 115. As such, the particulate filter 115 can be of any type and have any rating adequate for the intended application, for example it can be a MERV 8 media filter (e.g., 7 inches by 7 inches by 1 inch thick), as depicted. In other embodiments, the particulate filter can be a HEPA filter, an electronic cleaner, or an electrostatic filter, a filter with antimicrobial coating, or multiple same-type or different particulate filters can be provided in series. The particulate filter 115 is held in place by conventional brackets that permit (with the housing cover lid removed) removing and replacing the filter 115 such as for periodic maintenance or changing out. The particulate filter 115 receives ambient air from the air intake 122 of the housing 102 and passes on pre-treated air to the antimicrobial filter 116 for further treatment, with the air flowing under the influence of the air mover 119.

The antimicrobial or germicidal filter 116 is selected for capturing airborne pathogenic cells and microbes and removing them from the airflow, and for killing, or at least significantly damaging and/or sterilizing, the pathogenic cells and microbes that are able to pass through it. Also, the antimicrobial filter 116 is selected for low airflow resistance, preferably to allow for a high airflow rate of about 140 to 150 cubic feet per minute, with airspeeds of about 437 feet per minute to about 468 feet per minute, through the filter 116. In typical embodiments, for example, the antimicrobial filter 116 is provided by a non-woven and pleated filter media treated with copper and silver molecules (e.g., embedded into or coated onto the media). The copper molecules lyse cell membranes of bacteria and the silver molecules disrupt DNA and result in microbial cell death. In other embodiments, only copper or silver is included, different materials with antimicrobial properties are included, additional antimicrobial materials are included along with copper and/or silver, or multiple same-type or different antimicrobial filters can be provided in series, for example a metal (e.g., copper or another metal) mesh filter with an antibacterial coating (the metal physically lyses the cells, which then come into contact with the silver or other antibacterial coating). The antimicrobial filter 116 is held in place by conventional brackets that permit (with the housing cover lid removed) removing and replacing the filter 116 such as for periodic maintenance or changing out. The antimicrobial filter 116 receives the pre-treated air from the particulate filter 115 and passes on the twice-filtered air from the pre-treating stage to the UV chamber 110 for further treatment, with the air flowing under the influence of the air mover 119.

In the depicted embodiment, the antimicrobial filter 116 is positioned upstream from the air mover 119 and the UV chamber 110, thereby keeping them from pathogen buildup and providing for more efficient airflow by allowing the air mover 119 to suck the air through with a higher pressure drop. In other embodiments, the antimicrobial filter 116 is positioned downstream from the UV chamber 110.

Figure 5:
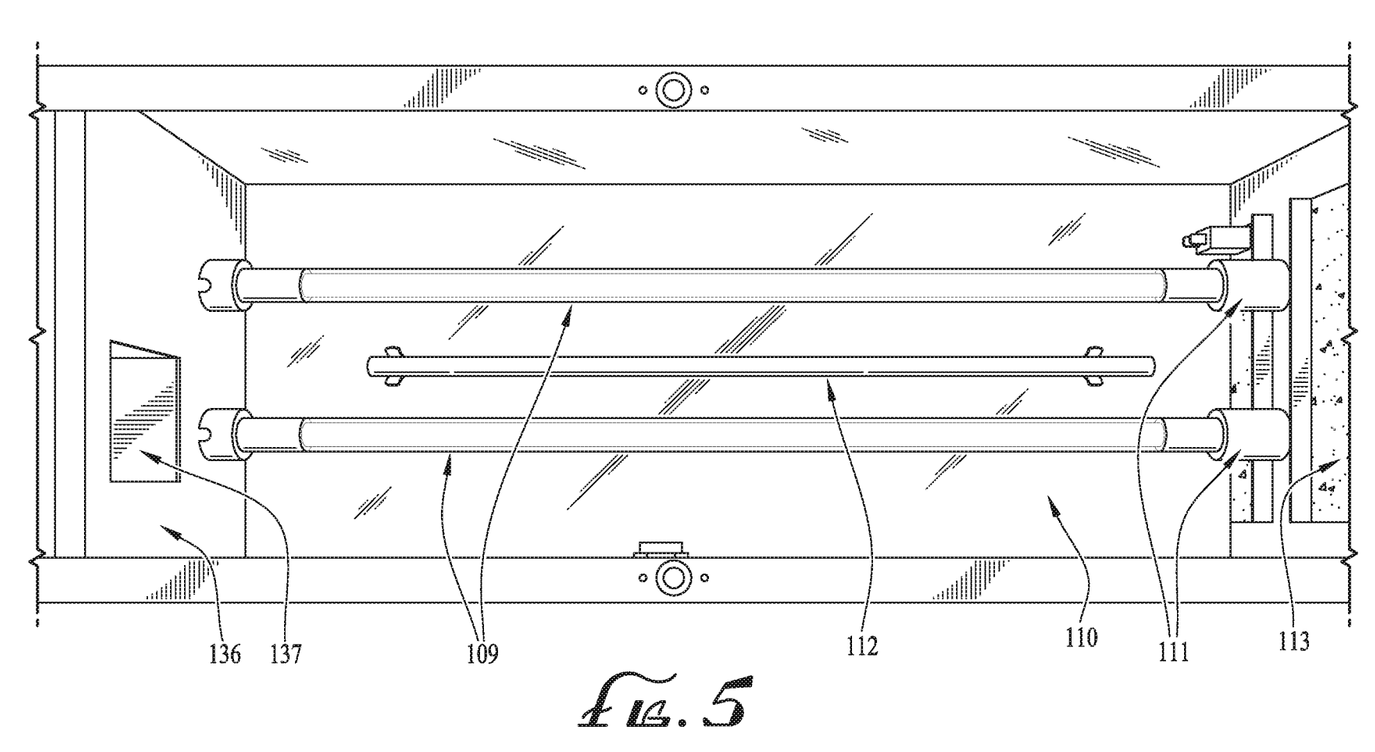
FIG. 5 is a plan view of the intermediate UV treatment chamber of the air treatment device of FIG. 1.

Referring additionally to FIG. 5, the UV chamber 110 contains one or more ultraviolet (UV) lamps 109 selected for producing UV light energy or radiation for killing any pathogens that escape and survive the antimicrobial filter 116. In the depicted embodiment, for example, there are two germicidal mercury vapor UV lamps, each 538 mm long and each rated at about 254 nm UV light at 25.6 W for producing UVC irradiation, with a design lifetime of up to 10,000 hours. In other embodiments, the UV lamps are selected with other ratings, for example, a wavelength sufficiently close to 254 nm UV that it's comparably effective at pathogen killing, about 100 nm to about 280 nm (UVC range), about 280 nm to about 320 nm (UVB range), in other numbers (one or three or more), and/or of different size and specification (e.g., different wavelength, UVA or UVB, different wattage, different size, lifetimes, etc.), depending on the intended application and desired design parameters.

Also, the UV lamps 109 can be mounted in spring-loaded lamp holders 111 for easy removal and replacement without the need for specialized tools.

In addition, the UV chamber 110 can be designed for amplifying and intensifying the UV irradiation from the UV lamps 109. For example, the UV chamber 110 can include a reflective lining to intensify the UV irradiation from the UV lamps 209. The reflective lining can be provided by sheets of a reflective material, for example a mirror-finish anodized aluminum or another reflective material known in the art and selected for multiplying the effects of the UV lamps 109 through reflection. Additionally, the UV chamber 110 can include one or more catalyst devices 112 that promote a photocatalytic reaction to create hydroxyl radicals, which can result in increased cell death of bacteria. The catalyst devices 112 can be provided by stainless steel reflective tubes (or bars or other reflective surface devices), for example optionally coated with titanium dioxide ($TiO_2$). In other embodiments, the catalyst devices can include another material for promoting a photocatalytic reaction to intensify the pathogen-killing efficacy of the device 100. The photocatalytic reaction of the UVC radiation with the TiO2 and the redirection of the UVC radiation by the reflective walls of the UV chamber act to slow the dissipation of the UVC energy. The UV chamber 110 receives the twice-filtered air from the pre-treating stage and passes on the UV-treated air to the post-UV stage.

Figure 6:
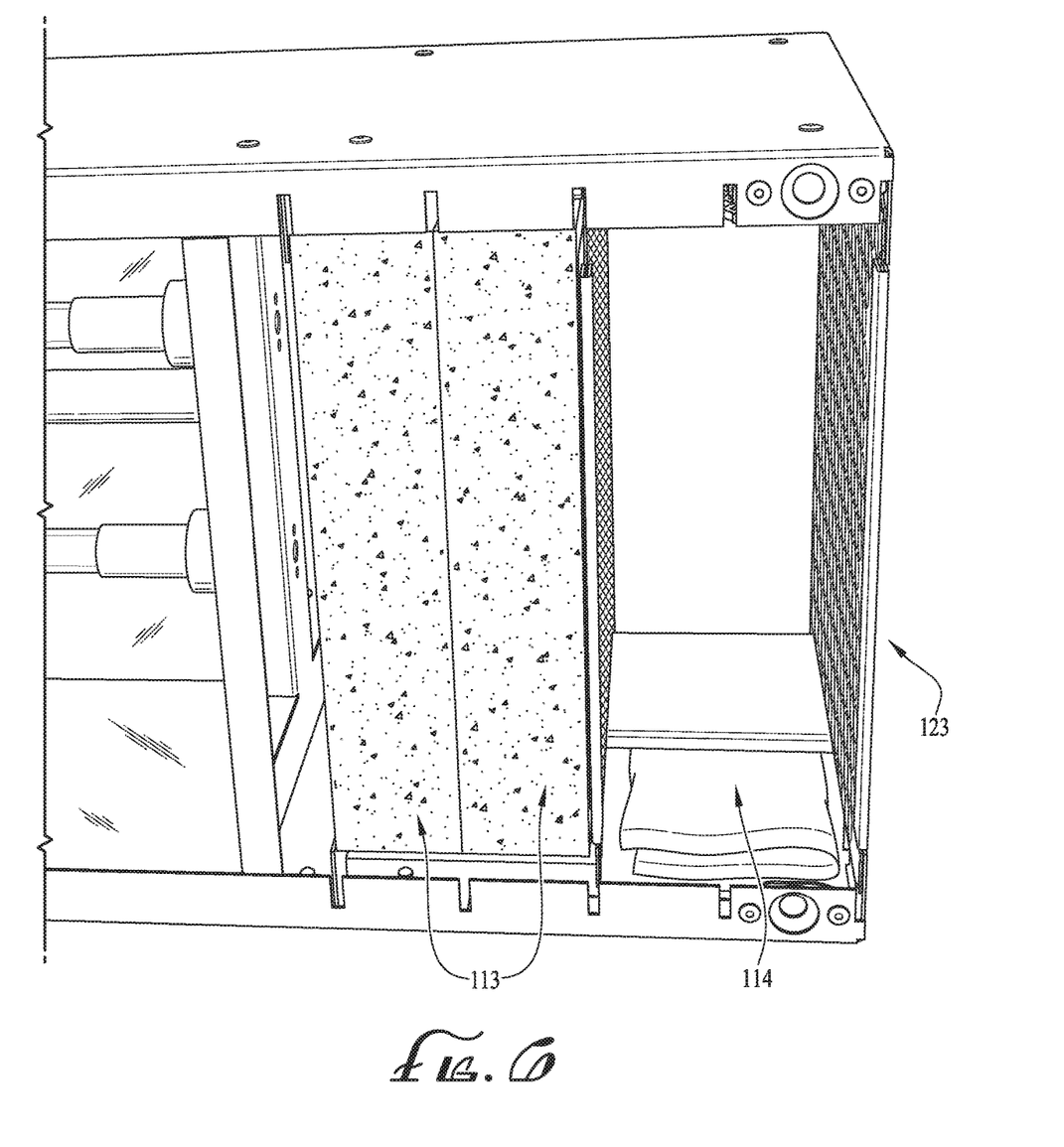
FIG. 6 is a plan view of the exit chamber of the air treatment device of FIG. 1.

Referring additionally to FIG. 6, the post-UV treatment stage will now be described. The post-UV treatment stage includes an exit chamber downstream from the UV chamber 110 and contains one or more VOC-reducing filters 113 selected for removing volatile organic compounds and odors such as terpenes from air. Also, the VOC-reducing filters 113 are selected for low airflow resistance, preferably to allow for a high airflow rate of about 140 to 150 cubic feet per minute, with airspeeds of about 437 feet per minute to about 468 feet per minute, through the filters 113. For example, the VOC-reducing filters 113 can be provided by two honeycomb-monolith filter media coated or otherwise treated with an odor-absorbing material, such as honeycomb-monolith (e.g., 200 cells per square inch) activated-charcoal filters, as depicted. The VOC-reducing filters 113 can be provided in conventional thicknesses with the number of filters selected for serial arrangement selected based on the filter area desired, the filters can be provided in custom thicknesses so a selected number (e.g., one) of the filters provides the desired filter area, and/or the filters can be provided with other honeycomb-cell sizes/densities (e.g., 50 or 100 cells per square inch). Also, the VOC-reducing filters 113 can be provided with honeycomb cells that are not uniformly and consistently arranged, so that for two or more serially positioned filters 113 the cells of adjacent filters do not axially align, which effectively blocks (at least some) transmission of UV light out of the UV chamber 110. In other embodiments, the VOC-reducing filters can be provided by other carbon filters, filters with oxidizing agents, filters with zeolite (aluminum, hydrated silicon compounds, and oxygen), filters with manganese dioxide and copper oxide (e.g., commercially available under the brand name CARULITE), other numbers of filters (e.g., one or three or more), or other filter types known in the art for removing VOCs and odors from air. The VOC-reducing filters 113 are held in place by conventional brackets that permit (with the housing cover lid removed) removing and replacing the filters 113 such as for periodic maintenance or changing out. In the depicted embodiment, the VOC-reducing filter 113 is positioned downstream from the UV chamber 110, but in some embodiments the VOC-reducing filter 113 can be positioned upstream from the UV chamber 110.

The VOC-reducing filter 113 receives the UV-treated air from the UV chamber 110 and passes on the VOC-treated air, either discharging it from the housing 102 through the discharge end 123, or delivering it for further treatment in embodiments so equipped. For example, the depicted embodiment includes an optional supply of a surface disinfectant 114 selected for dispersal into and carrying by the air so that after discharge form the housing 102 it settles on any nearby ambient surfaces and prevents surface colonization and contamination from any surviving microorganisms in the discharged air. For example, the surface disinfectant supply 114 can be provided by chlorine dioxide ($ClO_2$) in a slow-release sachet.

In other embodiments, the surface disinfectant supply can be provided by another material known in the art for dispersal into air and disinfecting surfaces and/or it can be provided in another delivery device, such as chlorine dioxide dissolved in water (e.g., commercially available under the brand name TWINOXIDE) and dispensed in an aerosol spray, a solution of liquid hydrogen dioxide dispensed in an aerosol spray, or a UV light photolysis device that produces and disperses hydrogen peroxide into the airflow. The surface disinfectant supply 114 can be provided in its own sub-chamber of the post-UV exit chamber, separated from a sub-chamber for the VOC-reducing filter 113 by a grating (e.g., a honeycomb, lattice, screen, or mesh plate), as depicted. As the air flows across the surface disinfectant supply 114, the disinfectant (e.g. chlorine dioxide) is dispersed into the air and discharged with the air out of the device 100 to settle on surfaces in the space whose air is being treated.

Figure 7:
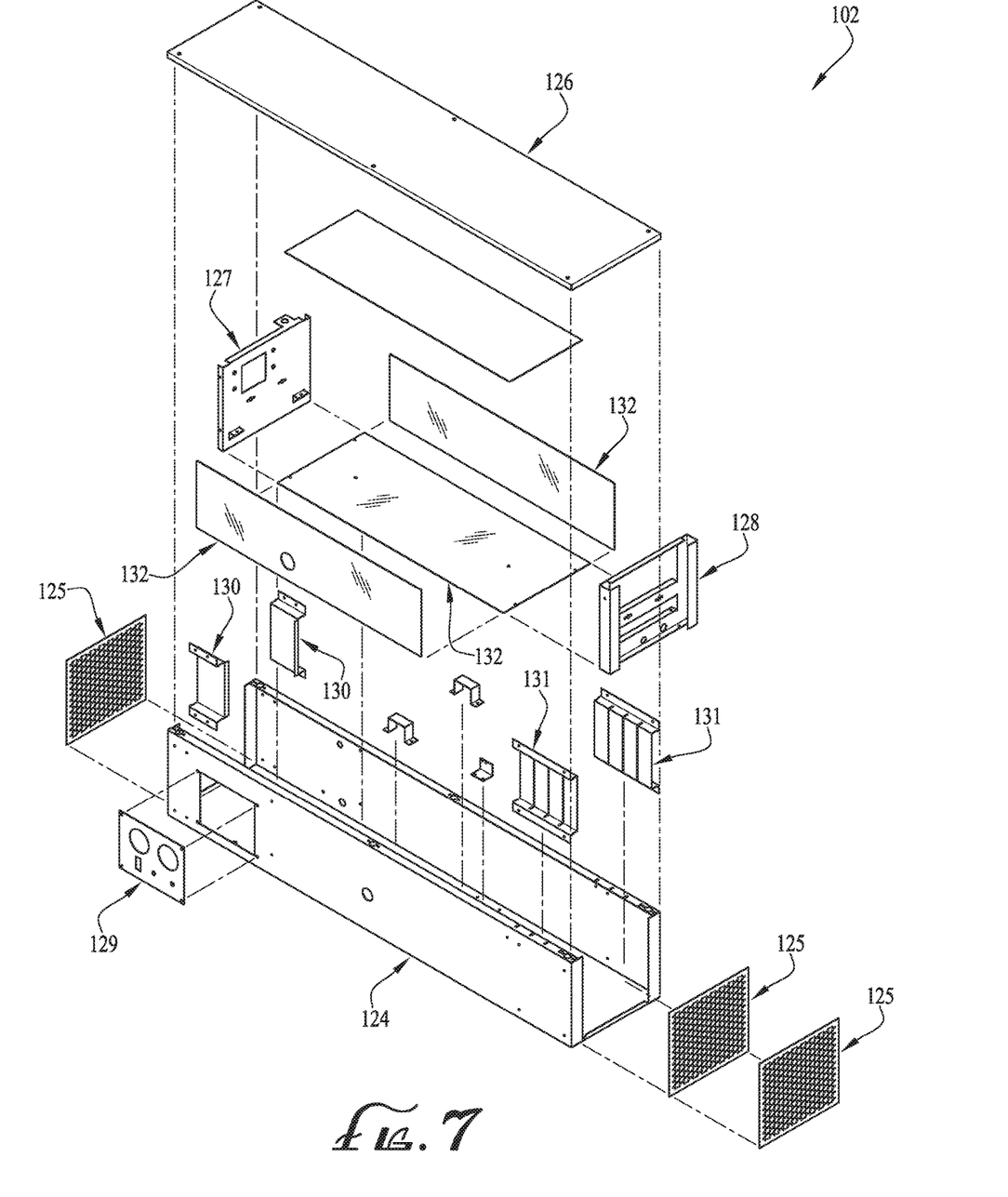
FIG. 7 is an exploded perspective view of the housing of the air treatment device of FIG. 1.

FIG. 7 shows the various parts of the example housing 102 of the air-treatment device 100. The housing can be of a conventional type for example a powder-coated galvanized-steel cabinet or plenum (as depicted) or another housing constructed to provide strength and durability to the device 100. The housing 102 can include a three-sided open-ended box 124, air-intake and air-discharge grating ends (e.g., honeycomb, lattice, screen, or mesh plates) 125, and a removable cover lid 126. The box 124 can include a plate 127 for attaching the blower (not shown) and a bracket 128 for holding the UV lamps (not shown) in place. The inlet-end portion of the housing 102 includes the control panel 129 and brackets 130 for holding the particulate and antimicrobial filters (not shown) in place. Brackets 131 for holding the VOC-reducing filters (not shown) are located at the discharge end portion of the housing 102. Reflective plates 132 line the three interior sides of the reflective chamber portion of the box 124 and the cover 126.

As noted above, the entrance/pre-treating chamber 133, the intermediate/UV chamber 110, the exit/post-UV chamber 134, as well as the air-handling chamber 135 containing the air mover 119, are all defined by and formed within the housing 102, and the unique design of the air treatment device 100 provides for high-efficiency air cleaning at very high airflow rates. As such, it should be noted that these individual chambers are effectively sections of the overall housing 102, without divider walls at their ends along the airflow route that would restrict the airflow. For example, the pre-treating chamber 133 has an entrance end that can be defined by the air intake 122 and an exit can be defined by the downstream surface of the antimicrobial filter 116 (or the downstream-most mounting bracket for it). The air-handling chamber 135 has an entrance end that can be defined by the downstream surface of the antimicrobial filter 116 (or the downstream-most mounting bracket for it) and an exit can be defined by an airflow opening 137 in a divider panel 136 of the housing 102. The intermediate/UV chamber 110 has an entrance end that can be defined by the airflow opening 137 in the divider panel 136 and an exit can be defined by the upstream surface of the VOC-reducing filter 113 (or the upstream-most mounting bracket for it). And the exit/post-UV chamber 134 has an entrance end that can be defined by the upstream surface of the VOC-reducing filter 113 (or the upstream-most mounting bracket for it) and an exit can be defined by the air discharge 123.

Also, in typical commercial embodiments, the air-handling chamber 135 is positioned after/downstream from the chamber 133 with the particulate filter 115 and the antimicrobial filter 116 (to protect the operational/control equipment from the removed/killed large particles and pathogens and to enable drawing/pulling the air through these filters) and before/upstream from the UV-chamber 110 (so the divider panel 136 and the air mover 119 block UV light transmission through the UV-chamber entrance). And the chamber 134 with the VOC-reducing filters 113 is positioned after/downstream of the UV-chamber 110 (so the VOC-reducing filters block (at least some) transmission of UV light through the UV-chamber exit, and so they remove ozone in some embodiments as described below).

Figure 8:
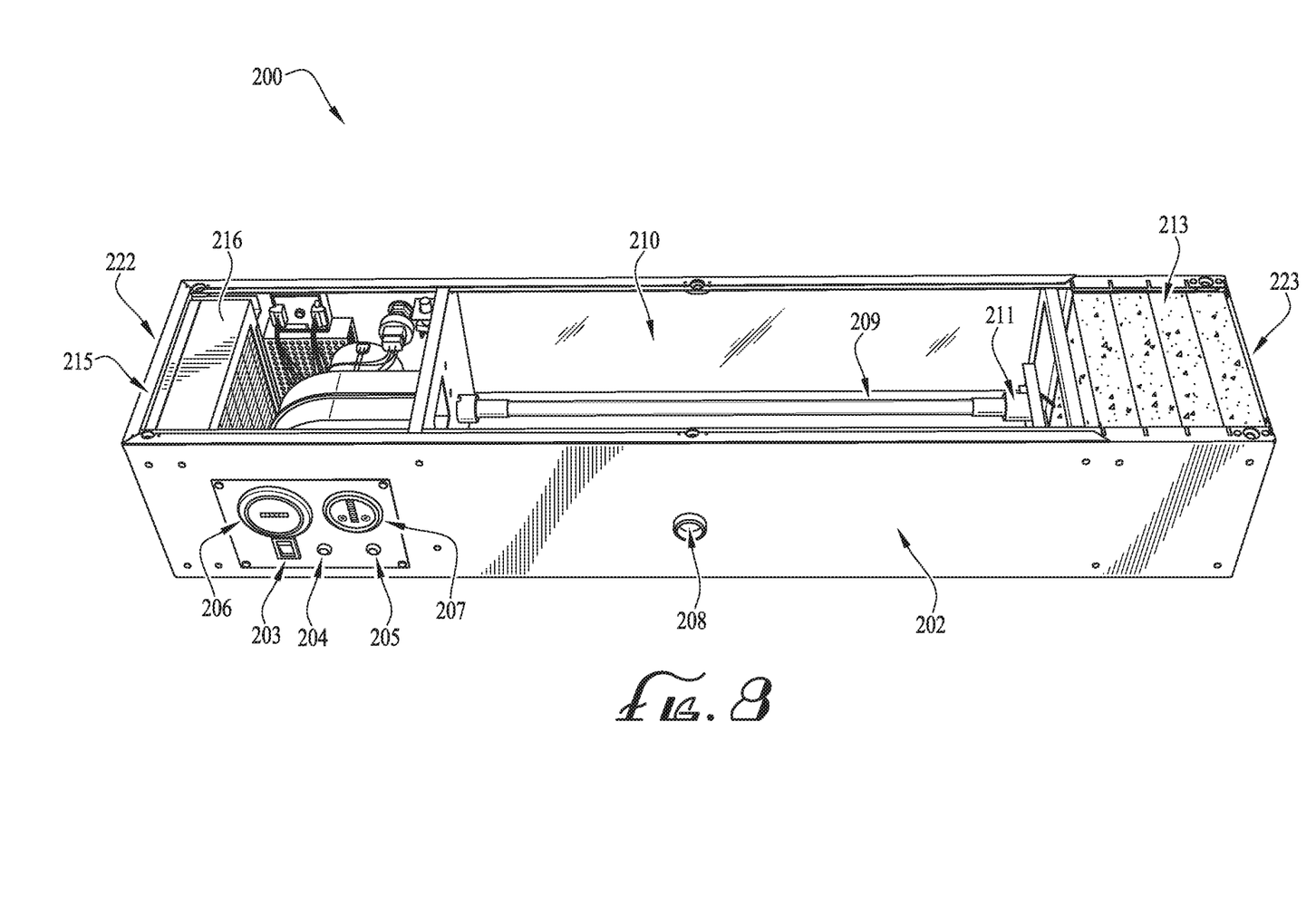
FIG. 8 is a perspective view of an air treatment device according to a second example embodiment of the present invention, with a cover panel of the housing removed to show the internal components, including an entrance treatment chamber, an intermediate UV treatment chamber, and an exit treatment chamber, configured for removing ethylene from the air.

Turning to FIG. 8, there is depicted is an air-treatment system or device 200 according to a second example embodiment of the present invention. The device 200 of this embodiment is similar to that of the above-described example embodiment in many aspects, but is configured for additionally removing ethylene from the air, for example by including lower-frequency UV lamps 209 and additional VOC-reducing filters 213. The device 200 components are housed in a housing 202 (e.g., a powder-coated galvanized steel box) designed and constructed for strength and durability. The device 200 includes a control panel with conventional user-interface control components, for example typical embodiments include an on/off power control (e.g., switch) 203, UV lamp status indicators (e.g., operative 204 and replacement-time 205 status), a run-time indicator (e.g., hour meter) 206, and a filter status indicator (e.g., efficiency meter) 207. Also, the device 200 typically includes a sight glass 208 through the housing 202 for viewing the inner reflective chamber 210, in similar fashion as the above-described example embodiment.

Air from the surroundings is drawn into the inlet 222 of the air-treatment device 200 by the air mover (e.g., blower), through the particulate filter 215 and the antimicrobial filter 216, and into the reflective chamber 210, in similar fashion as described above. The particulate filter 215 can be selected with a rating for the particular application, for example in typical embodiments a MERV 8 filter is used. The particulate filter 215 aids in removing relatively large airborne particles such as dust and pollen, thereby helping prevent the downstream antimicrobial filter 216 from clogging with these particulates. In addition, the antimicrobial filter 216 can be selected to provide for killing, or at least significantly damaging, pathogenic cells and microbes that pass through it. In typical embodiments, for example, the antimicrobial filter 216 is provided by a non-woven, pleated, filter medium, with copper and/or silver molecules embedded in the media. The copper molecules can lyse cell membranes of bacteria and silver molecules can disrupt DNA and result in microbial cell death.

The pre-treated air is then introduced into the reflective chamber 210 where it is exposed to irradiation from one or more UV lamps 209. The number and rating of the UV lamps 209 are selected for the particular application. For example, in typical embodiment there are two short-wave UVC lamps each rated at about 180 nm UV, 25.6 W, for removing ethylene from the air. In other embodiments, the reflective chamber 210 includes one or three or more UV lamps, and/or UV lamps with other wavelength ratings (e.g., UVA or UVB) and/or wattages (e.g., a wavelength sufficiently close to 180 nm UV that it's comparably effective at producing ozone), depending on the intended application and desired design parameters. The low UVC irradiation can kill any pathogens that survive the antimicrobial filter 216. Also, the low UVC radiation produces ozone, which is a potent pathogen killer and thus contributes to the killing efficacy of the device 200. In addition, the ozone reacts with any ethylene gas present in the air to produce carbon dioxide and water, thereby reducing ethylene levels in the treated space.

The reflective chamber 210 optionally also includes one or more catalyst devices for intensifying the UV irradiation from the UV lamps 209. In typical embodiments, the catalyst devices can be provided by stainless steel reflective tubes (or bars or other reflective surface devices) (not shown in this view), for example optionally coated with titanium dioxide, which promotes a photocatalytic reaction to create hydroxyl radicals, which can result in cell death of bacteria that escaped the antimicrobial filter 216. In addition, the reflective chamber 210 in typical embodiments is lined with a reflective material, for example a mirror-finish anodized aluminum, to amplify the effects of the UV lamps 209 through reflection. Also, the UV lamps 209 can be mounted in spring-loaded lamp holders 211 for easy replacement.

The UV-treated air then passes through one or more VOC-reducing filters 213 and is discharged out through housing discharge end 223 back to the ambient environment. In typical embodiments, for example, the VOC-reducing filters 213 are provided by four activated-charcoal odor-control filters for removing odors and ozone from the air before it leaves the device 200, and for applications including removing ethylene from the air. In other embodiments, more or fewer VOC-reducing filters can be used, and/or VOC-reducing filters of another type. In this embodiment, the VOC-reducing filter 213 is positioned downstream from the UV chamber 210 in order to remove ozone produced by the UV lamps 209.

In another aspect of the invention, there are provided methods of treating air to remove pathogens and contaminants. The descriptions herein of the air treatment devices 100 and 200 include details not only of their construction but also of methods of their use to treat the air. Accordingly, the above descriptions of air treatment devices of the invention include descriptions of air treatment methods of the invention, and details of such methods are not repeated.

Test Example

The following test example is included to provide those of ordinary skill in the art with a complete disclosure and description of how the systems and methods described herein are made and evaluated, and is intended to be purely exemplary and is not intended to limit the scope of what the inventors regard as their invention. Efforts have been made to ensure accuracy with respect to numbers (e.g., amounts, temperatures, etc.), but some errors and deviations should be accounted for. Unless indicated otherwise, parts are parts by weight, temperature is in degrees F. or is at ambient temperature, and pressure is at or near atmospheric. Numerous variations and combinations of reaction conditions (e.g., temperatures, pressures, and other reaction ranges and conditions) can be used to optimize the described process. Only reasonable and routine experimentation will be required to optimize such processes and conditions.

Test Example: Testing Procedure

The device 100 for removing pathogenic microorganisms from the air, in the typical configuration described above, was used to determine the clean air rate (microbial; CARm) for the device when challenged with microbial aerosols. This was accomplished by comparing the natural decay rates of the microorganisms (i.e., with the device off) to the decay rates of those microorganisms with the device on.

The device 100 was placed into a dynamic microbiological test chamber on a cart at a height of about 3 feet above the floor. The test chamber was a room-sized (2.44 m×2.44 m×3.05 m, or 640 ft$^3$) environmental chamber that is nominally a Class 1,000 cleanroom. The chamber contained a ceiling-mounted mixing fan with two aluminum blades 61 cm in diameter and attached to a shaft extending 61 cm down from the ceiling in the center of the chamber. Temperature and relative humidity for all of the test runs averaged 72±1° F. and 35±2%, respectively.

Challenge microorganisms were selected for testing as follows:

*Staphylococcus epidermidis*: a gram positive bacteria that serves as a stimulant for *S. aureus*, which is commonly associated with nosocomial infections and methicillin-resistant *Staphylococcus aureus* (MRSA).

*Bacillus atrophaeus*: a stimulant for *B. anthracis* with a spore form that is resistant to inactivation.

MS2 bacteriophage: a common viral stimulant for mammalian viruses such as influenza and norovirus.

Bioaerosol suspensions were aerosolized using a collison nebulizer (BGI, Waltham, Mass.) attached to a drying tower. The aerosol was generated at 15 psi and the drying tower supplied 3.5 SCFM of HEPA-filtered drying air. Three sampling ports designated A, B, and C were used to collect triplicate simultaneous samples. Port A was positioned near the center of the chamber wall, 1.52 m above the chamber floor and 1.0 m from the chamber wall. Port B was positioned 1.52 m above the chamber floor but was 0.25 m from the front wall of the chamber. And port C was positioned directly below Port A and 0.65 m above the chamber floor. Sampling of the bioaerosols was accomplished using either a single-stage ANDERSEN viable bioaerosol sampler or an all-glass impinger (AGI-4).

The *S. epidermidis* and *B. atrophaeus* used the single-stage sampler which allowed for direct collection of the bioaerosol challenge onto petri dishes containing solid media appropriate for the specific microorganism. Colony forming units (CFU) were counted and recorded. Bacteriophage MS2 utilized the AGI-4 units, which contained 20 mL of impinger fluid. The collected viral particles were counted for plaque forming units (PFU) on a lawn of *E. coli*.

The following test protocol was used:
(1) The chamber ventilation system and ceiling fan were turned on.
(2) A HEPA filter was allowed to clean the chamber air for at least one hour.
(3) The ventilation system was turned off and the collison nebulizer was turned on and run for 5 min with the HEPA-filtered drying air flowing at 3SCFM.
(4) The collison nebulizer and drying air were stopped, and the chamber air was mixed using the ceiling fan for 1 min.
(5) The ceiling fan was turned off and a "time 0" sample was obtained.
(6) Triplicate bioaerosol measurements were collected at time lapses of 5, 10, and 15 mins (in 5 min intervals).

(7) The chamber was cleaned for 20 min using the ventilation system with the ceiling fan on.
(8) Steps 3-7 were repeated with the air-treatment device 100 turned "on" after step 5.

Test Example: Calculations

The performance of the air treatment device 100 was evaluated by determining the clean air rate (microbial) or CARm, calculated as the CADR in the AHAM method. To calculate the CARm, the measured decay ($k_e$) (device 100 on) and natural decay ($k_n$) (device 100 off) rates are first calculated using the following formula:

$$k = \frac{\left(\sum t \times \ln C_t\right) = \left[\sum t)\left(\sum \ln C_t\right)\right]/n}{(\sum t^2) - (\sum t)^2/2}$$

where:
$C_t$=concentration at time t;
n=number of data points used in the regression;

k=decay constant ($time^{-1}$); and t=time (min.).

Then the CARm was calculated for each measured decay rate using the following formula:

$$CARm=Vk_e-k_n$$

where:

V=volume of the test chamber ($ft^3$);

$k_e$=measured decay rate ($min^{-1}$); and $k_n$=average natural decay rate ($min^{-1}$) for an organism.

Test Example: Microbial Decay Rates

Figure 9:
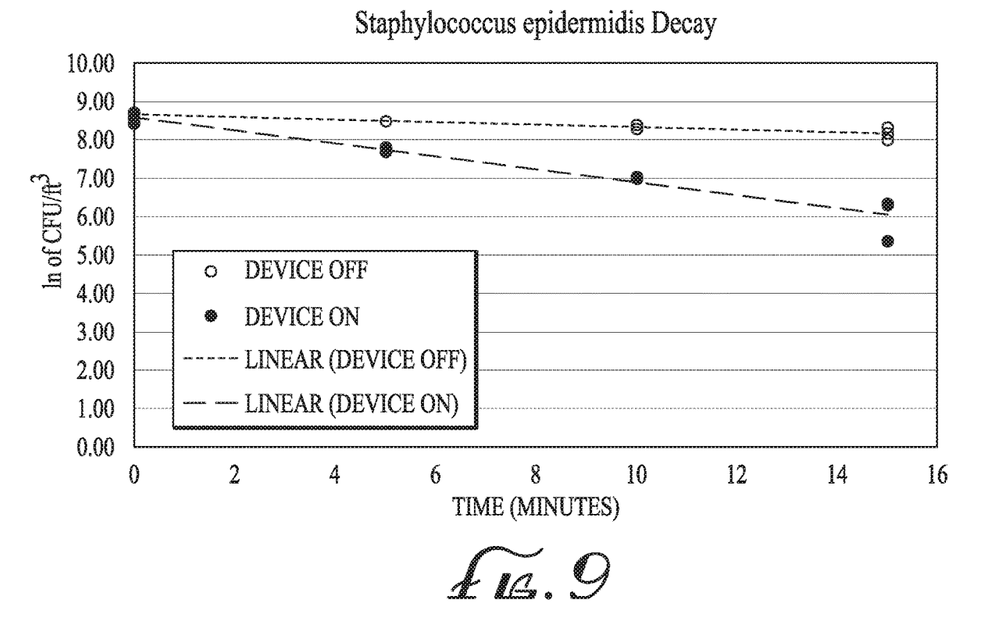
FIG. 9 shows a comparison of decay rates of *Staphylococcus epidermidis* with and without the operation of the air treatment device of FIG. 1.
Figure 10:
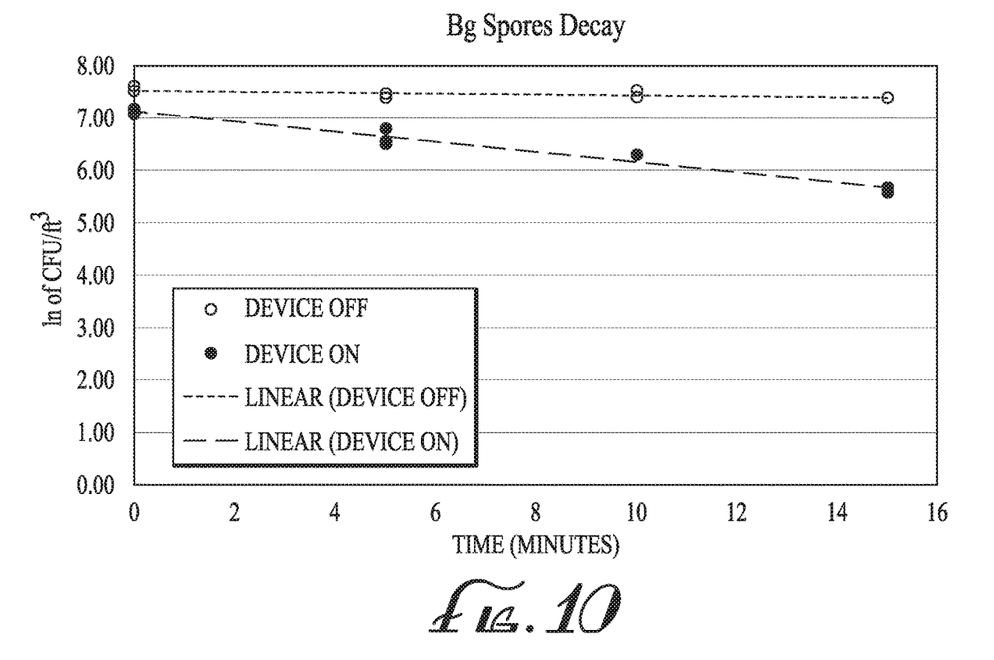
FIG. 10 shows a comparison of decay rates of *Bacillus atrophaeus* (Bg) spores with and without the operation of the air treatment device of FIG. 1.
Figure 11:
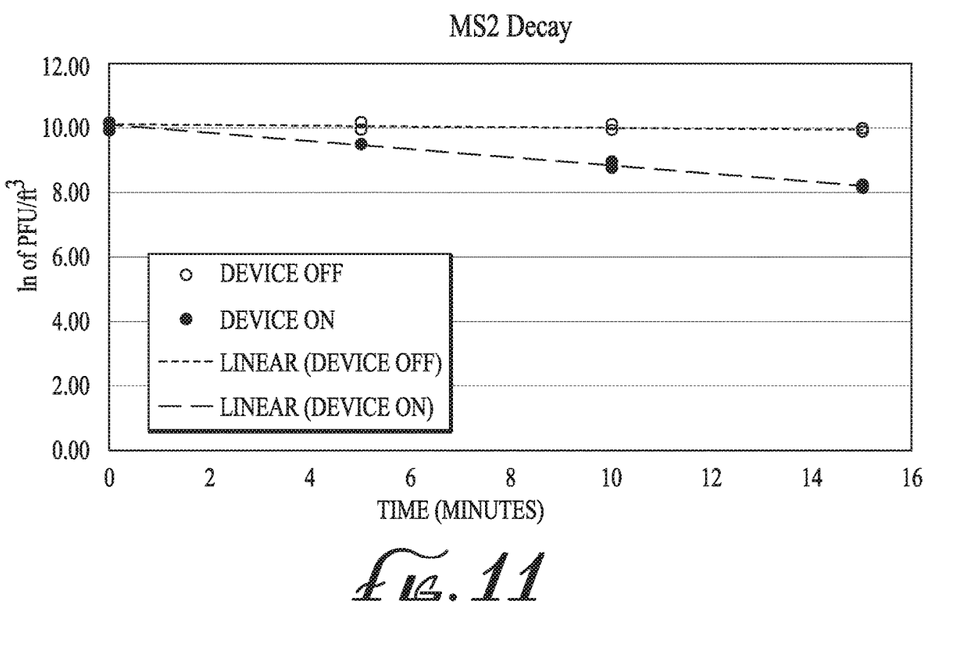
FIG. 11 shows a comparison of decay rates for bacteriophage MS2 with and without the operation of the air treatment device of FIG. 1.
Figure 12:
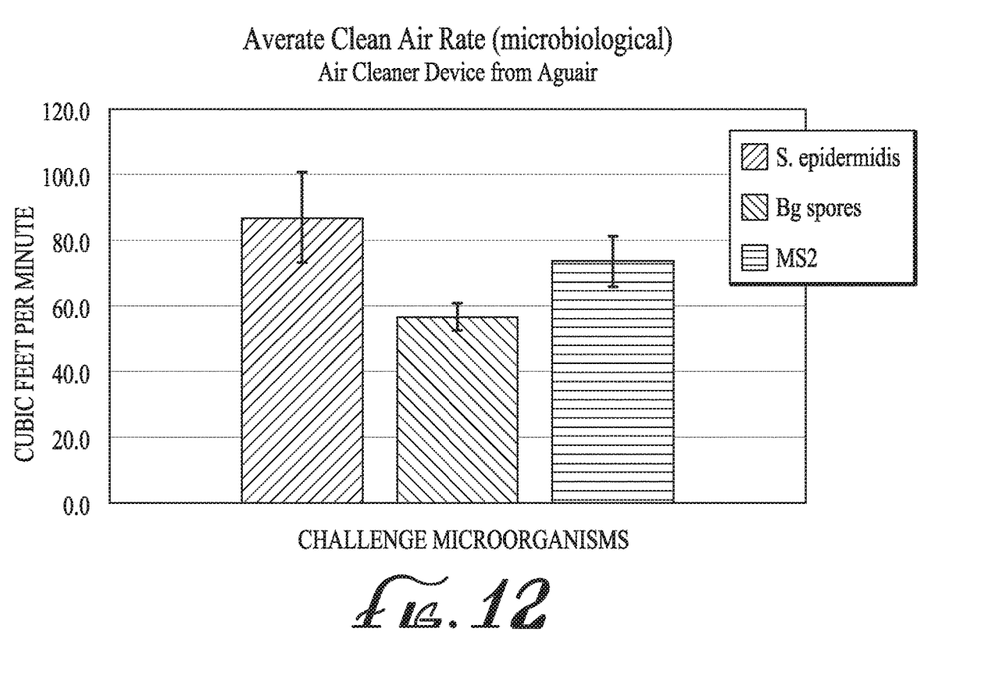
FIG. 12 is a graph of the average clean air rate using the air treatment device of FIG. 1.

The decay curves for each of the microorganisms used to challenge the air-treatment device 100 are shown in FIGS. 9-11. The numbers of CFUs or PFUs per cubic foot in the test chamber are plotted on the y-axis versus the time in minutes on the x-axis. The data points for each time represent average results from the three sampling locations, with natural decay curves being labeled "Device OFF" and air cleaner decay curves labeled "Device ON." FIG. 9 shows the decay curves for *S. epidermidis*, FIG. 10 shows the decay curves for Bg spores, and FIG. 11 shows the decay curves for bacteriophage MS2.

All of the challenge microorganisms showed an increase in decay rates with the air-treatment device 100 on compared to their natural decay. This was evident based on the slopes of the linear regressions. The measured decay rates calculated according to the CARm method for each organism are shown in Table 1:

TABLE 1

Decay rates measured for introduced microbial aerosols

| | Device OFF | | Device ON | |
|---|---|---|---|---|
| | $k_n$ | standard deviation | $k_e$ | standard deviation |
| *Staphylococcus epidermidis* | −0.0328 | 0.0046 | 0.1687 | 0.0138 |
| Bg spores | −0.0086 | 0.0032 | 0.0972 | 0.0138 |
| MS2 | −0.0093 | 0.0048 | 0.1244 | 0.0045 |

Table 2 presents the average CARm results and standard deviations. The CARm was calculated as shown above and is a comparison of the two decay rates (natural and aid cleaner) as a function of the volume of the test chamber. These results are also displayed graphically in FIG. 12.

TABLE 2

CARm values calculated from mean decay rates

| | *S. epidermidis* | Bg spores | MS2 |
|---|---|---|---|
| CARm (cfm) | 87.0 | 56.7 | 73.7 |
| standard deviation | 13.6 | 4.0 | 7.7 |

Assuming the same room conditions, including lack of leaks, no sources of organisms other than the initial injection, and size, and looking only at the influence of the air-treatment device 100 (actual removal level would be slightly higher due to, for example, gravity), the predicted removal/inactivation levels of organisms over one hour are shown in Table 3.

TABLE 3

Predicted removal level in one hour of continuous use

| | *S. epidermidis* | Bg spores | MS2 |
|---|---|---|---|
| Removal/Inactivation Level (%) | 99.97 | 99.51 | 99.90 |

As can be seen from the above results, in the ideal case where the air-treatment device 100 provides a well-mixed chamber, the CARm is equivalent to the product of the air-treatment device's flow rate and its filtration efficiency for the challenge bioaerosol. In a chamber test, however, the test chamber is only "well-mixed" to the extent that air-treatment device 100 itself provides this mixing by the air motions generated by its fan. Thus, the CARm combines the effects of filtration efficiency of the air-treatment device 100 and the effectiveness of the air-treatment device 100 to draw the test chamber's air through it. Generally, the CARm will not exceed the air-treatment device's 100 flow rate. This air-treatment device 100 has been shown to inactivate all three challenge organisms with different efficacies depending on the organism.

While the invention has been described with reference to example embodiments, it will be understood by those skilled in the art that a variety of modifications, additions, and deletions are within the scope of the invention, as defined by the following claims.

What is claimed is:

1. A device for treating air in a contained space where food is stored or processed, the air treatment device comprising:

a housing through which the air flows and including an intake that receives the air from the contained space, a pre-treatment chamber downstream from the intake, an air-handling chamber downstream from the pre-treatment chamber, a UV-treatment chamber downstream from the air-handling chamber, a post-UV-treatment chamber downstream from the UV-treatment chamber, and a discharge that returns the air to the contained space;

a pre-treating stage that includes a particulate filter and an antimicrobial filter contained within the pre-treatment chamber, wherein the particulate filter is a media filter that removes airborne particulate contaminants from the air, the antimicrobial filter is a nonwoven pleated filter media treated with antimicrobial materials that removes pathogens from the air and/or damages any pathogens that are not removed from the air;

an air mover that forces the air to flow through the housing from the intake to the discharge, wherein the air mover is contained within the air-handling chamber and positioned upstream from the UV-treatment chamber;

at least one ultraviolet lamp and a catalytic device contained in the UV-treatment chamber, wherein the at least one ultraviolet lamp emits UV radiation that kills any of the pathogens that are not removed from the air, and the catalytic device produces a photocatalytic reaction that kills any of the pathogens that are not removed from the air;

a post-UV stage that includes a VOC-reducing filter and supply of a surface disinfectant that are contained within the post-UV-treatment chamber, wherein the VOC-reducing filter removes VOCs and odors from the air, and the surface disinfectant includes chlorine dioxide that is picked up by the air and discharged from the housing to settle on nearby ambient surfaces to prevent surface colonization and contamination from any surviving pathogens in the discharged air, wherein the UV-treatment chamber is defined by sidewalls, a divider panel at an upstream end, and the VOC-reducing filter at an opposite downstream end, wherein the UV-treatment chamber sidewalls and divider panel include a reflective lining to intensify the UV radiation emitted by the at least one ultraviolet lamp, wherein the divider panel includes an airflow opening and is positioned between the air mover and the at least one ultraviolet lamp, and the air mover is mounted in place with an outlet of the air mover abutting the divider panel at its airflow opening so that the air mover forces air through the divider panel airflow opening and into the UV-treatment chamber while the divider panel and the air mover block upstream transmission of the UV radiation, wherein the VOC-reducing filter includes a honeycomb-monolith filter media treated with an odor-absorbing material that removes ozone introduced into the air by the at least one ultraviolet lamp, blocks downstream transmission of the UV radiation, and enables the air to flow out of the UV-treatment chamber, and wherein the particulate filter and the antimicrobial filter clean the air by filtration, the at least one ultraviolet lamp cleans the air by killing the airborne pathogens, and the particulate filter, the antimicrobial filter, the air mover, and the VOC-reducing filter are selected so that the air mover forces the air through the particulate filter, the antimicrobial filter, the UV-treatment chamber, and the VOC-reducing filter at an airflow speed of about 437 feet per minute to about 468 feet per minute.

2. The air treatment device of claim 1, wherein the antimicrobial filter has a finer pore size than the particulate filter, and the particulate filter is positioned upstream in the airflow from the antimicrobial filter and the air mover, wherein the airborne particulate contaminants in the air do not clog the antimicrobial filter or damage the air mover.

3. The air treatment device of claim 2, wherein the antimicrobial filter is positioned upstream in the airflow from the air mover, wherein the pathogens in the air do not contaminate the air mover.

4. The air treatment device of claim 1, wherein the antimicrobial filter includes silver material, copper material, or both.

5. The air treatment device of claim 1, wherein the at least one ultraviolet lamp emits UV radiation at a wavelength in a UVC range of about 100 nm to about 280 nm.

6. The air treatment device of claim 1, wherein the catalytic device includes titanium dioxide that produces free hydroxyl radicals to kill the pathogens that are not removed from the air.

7. The air treatment device of claim 1, wherein the VOC-reducing filter includes activated carbon.

* * * * *